United States Patent
L. De Oliveira Pombeiro et al.

(10) Patent No.: US 10,246,397 B2
(45) Date of Patent: Apr. 2, 2019

(54) PROCESS FOR PRODUCTION OF KETONES FROM SECONDARY ALCOHOLS

(71) Applicants: INSTITUTO SUPERIOR TÉCNICO, Lisbon (PT); INSTITUTO SUPERIOR DE ENGENHARIA DE LISBOA, Lisbon (PT); UNIVERSIDADE DO PORTO, Oporto (PT)

(72) Inventors: Armando Jose L. De Oliveira Pombeiro, Lisbon (PT); Luisa Margarida Dias R. De Sousa Martins, Lisbon (PT); Ana Paula Da Costa Ribeiro, Lisbon (PT); Sonia Alexandra Correia Carabineiro, Montijo (PT); Jose Luis Cabral Da Conceicao, Matosinhos (PT)

(73) Assignees: Instituto Superior Tecnico (PT); Instituto Superior De Engenharia De (PT); Universidade Do Porto (PT)

( * ) Notice: Subject to any disclaimer, the term of this patent is extended or adjusted under 35 U.S.C. 154(b) by 0 days.

(21) Appl. No.: 16/066,540

(22) PCT Filed: Dec. 22, 2016

(86) PCT No.: PCT/PT2016/000019
§ 371 (c)(1),
(2) Date: Jun. 27, 2018

(87) PCT Pub. No.: WO2017/116253
PCT Pub. Date: Jul. 6, 2017

(65) Prior Publication Data
US 2019/0002384 A1    Jan. 3, 2019

(30) Foreign Application Priority Data

Dec. 29, 2015   (PT) .......................... 109062

(51) Int. Cl.
| | | |
|---|---|---|
| C07C 45/29 | (2006.01) |
| B01J 31/00 | (2006.01) |
| C07C 49/403 | (2006.01) |
| C07C 49/78 | (2006.01) |
| B01J 31/18 | (2006.01) |

(52) U.S. Cl.
CPC ......... *C07C 49/403* (2013.01); *B01J 31/1815* (2013.01); *C07C 45/29* (2013.01); *C07C 49/78* (2013.01); *B01J 2231/70* (2013.01); *B01J 2523/842* (2013.01)

(58) Field of Classification Search
CPC .. C07C 45/29; B01J 31/1815; B01J 2523/842
See application file for complete search history.

(56) References Cited

PUBLICATIONS

L.M.D.R.S. Martins, et al., Highly efficient and reusable CNT supported iron (ii) catalyst for microwave assisted alcohol oxidation, Dalton Transactions, 2016, 4, 45, Dalton Trans., 2016.
Rajender S. Varma and Rajender Dahiya, Microwave-assisted oxidation of alcohols under solvent-free conditions using clayfen, Pregamon, 1997.
L.M.D.R.S Martins, et al., Heterogenisation of a c-scorpionate Fe(ii) complex on carbon materials for cyclohexane oxidation with hydrogen peroxide, Chemcatchem, 2013.

*Primary Examiner* — Sikarl A Witherspoon
(74) *Attorney, Agent, or Firm* — The Watson IP Group, PLC; Jovan N. Jovanovic

(57) ABSTRACT

The present invention relates to the process for production of ketones from secondary alcohols by the use of a hybrid material, formed by the dichlorohydrotris(pyrazol-1-yl) methane iron (II) complex covalently bound to multi-walled carbon nanotubes functionalized with superficial carboxylate groups, as efficient and selective catalyst of peroxidative oxidation, microwave-assisted and without solvent addition.

7 Claims, No Drawings

PROCESS FOR PRODUCTION OF KETONES FROM SECONDARY ALCOHOLS

FIELD OF THE INVENTION

Technical Field of the Invention

The present invention relates to the process for production of ketones from secondary alcohols by the use of a hybrid material, formed by the dichlorohydrotris(pyrazol-1-yl) methane iron (II) complex covalently bound to multi-walled carbon nanotubes functionalized with superficial carboxylate groups, as efficient and selective catalyst of the peroxidative oxidation, microwave-assisted and without solvent addition.

State of the Art

Recently, chemical processes of industrial production have been the centre of profound transformations to fulfil sustainability criteria, where methods developed according to green chemistry principles are preferred over old methods [1-12]. One embodiment of this consists on the development of efficient, selective, environmentally tolerable and economically viable partial oxidation catalytic processes [1-12], that have attracted much attention of the scientific community. Among these, partial oxidation of alcohols and ketones stands out, not only due to functionalization relevance, but also by the important applications of the obtained ketones [1,2,4,7-9,13-15].

Regarding known synthetic processes, the majority needs high amounts of catalyst [16,17], long reaction times [18-20] and/or additives (bases, phase transfer agents, etc.) [2,16-20], as well as oxidants (e.g. manganese salts, chromates) [13-15,21,22] and solvents [19-24] which are often costly and/or toxic. The formation of by-products is another difficulty. Moreover, the catalysts used are frequently difficult to prepare, do not show good activity in the oxidation of aliphatic alcohols and are not possible to reuse [2,4,18-20, 25,26].

Therefore, there is still a need for new catalytic processes for alcohol partial oxidation that can mitigate some of the important above-mentioned limitations and although recently much work directed to these problems has been developed (namely the use of microwaves) [1,2,4], new solutions are needed.

The technical problem on the basis of the present invention is to provide a catalytic system of high efficacy and selectivity that allows the partial oxidation of secondary alcohols into respective ketones, in a sustainable way.

The present invention solves this problem by providing a process for production of ketones from secondary alcohols, using an efficient and reusable catalyst made of a hybrid material, on the basis of dichlorohydrotris(pyrazol-1-yl) methane iron (II) complex anchored in carbon nanotubes functionalized with superficial carboxylate groups, without solvent addition and using low-power microwave irradiation.

The hybrid material of the present invention acts in heterogeneous catalytic conditions, being particularly stable and easily separable from the reaction medium, but shows properties of homogeneous catalytic systems, namely with respect to selectivity and activity.

The advantages of this invention are due to the use of the above-described hybrid material in the microwave-assisted synthesis of ketones that allows to (i) create an almost quantitative conversion of the alcohol into ketone; (ii) reuse said hybrid material in a significant number of consecutive catalytic cycles without activity loss; (iii) eliminate the use of organic solvents; and (iv) reduce significantly the reaction time to 1 h.

It is therefore a simple, fast and ecological process significant in green chemistry.

Before the filing of this application, it was not known any application of hybrid materials constituted by iron complexes, with scorpionate ligands or others, anchored in multi-walled carbon nanotubes, as catalysts of oxidation processes of alcohols into ketones.

It was now surprisingly shown that the use of hybrid material formed by dichlorohydrotris(pyrazol-1-yl)methane iron (II) complex covalently bound to multi-walled carbon nanotubes functionalized with superficial carboxylate groups in the oxidation of secondary alcohols is a high efficacy and selectivity system on very short reaction times, and that can easily be reused without activity loss. An almost quantitative conversion of the alcohols into respective ketones for at least 6 consecutive cycles was achieved.

Although the dichlorohydrotris(pyrazol-1-yl)methane iron (II) complex has been applied on cyclohexane oxidation in homogeneous medium [27] and heterogeneous medium [32], none is described in the prior art that predicted the possibility of being used as active and selective catalyst of microwave-assisted, peroxidative oxidation of secondary alcohols into ketones. In fact, the hybrid material used in the present invention was shown to be surprisingly robust in the operative conditions used in the present invention (e.g., moderate temperatures up to 100° C. and under microwave irradiation), allowing its recycling and reuse for a number of successive catalytic cycles.

Taking into consideration the above-mentioned advantages, the catalytic process now developed, resulting from using the above-mentioned hybrid material, looks very promising in the economic point of view and with great potential to be industrially applied.

SUMMARY OF THE INVENTION

The present invention relates to the process for production of ketones from secondary alcohols by the innovative use of a hybrid material, made of dichlorohydrotris(pyrazol-1-yl) methane iron (II) complex covalently bound to multi-walled carbon nanotubes functionalized with superficial carboxylate groups, for the partial oxidation of 1-phenylethanol or cyclohexanol with tert-butyl hydroperoxide in the absence of solvents, with reduced reaction times, and using low-power microwave irradiation.

Thus, the present invention results from the unprecedented use of the above-mentioned hybrid material, as catalyst of the microwave-assisted, secondary alcohol oxidation that is easily separated from the reaction medium and reused in a new catalytic cycle without activity loss. This happens for at least six consecutive catalytic cycles.

The ketones synthesis route of the present invention prevents one of the most significant limitations of the use of homogeneous catalysts, i.e., the impossibility of separation from the reaction medium, while the hybrid material keeps the important characteristics of high activity and selectivity.

DETAILED DESCRIPTION OF THE INVENTION

The invention relates to a process for production of ketones from secondary alcohols by the use and mixture of a hybrid material, formed by the dichlorohydrotris(pyrazol- 1-yl)methane iron (II) complex covalently bound to multi-walled carbon nanotubes functionalized with superficial carboxylate groups, with iron content between 1 and 5% (w/w), as efficient and recyclable catalyst of partial oxidation of secondary alcohols, with tert-butyl hydroperoxide, as oxidising agent, at a temperature between 60 and 100° C. and microwave irradiation for one hour, into respective ketones, the process being carried out in environmentally tolerable conditions (no solvents and moderate temperatures) and with high yield and selectivity.

It was now shown that the use of the hybrid material formed by the dichlorohydrotris(pyrazol-1-yl)methane iron (II) complex covalently bound to multi-walled carbon nanotubes functionalized with superficial carboxylate groups in the oxidation of 1-phenylethanol or cyclohexanol is a high efficacy and selectivity system on very short reaction times, and that it can easily be reused without activity loss. Quantitative conversion of the alcohols into respective ketones for at least 6 consecutive cycles was achieved, with frequencies of catalytic cycles, i.e., turnover frequencies (TOF), expressed in moles of product per mole of catalyst per hour, up to $1.8 \times 10^3$ $h^{-1}$.

The advantages associated with this invention are due to the use of the above-described hybrid material in the process of microwave-assisted, synthesis of ketones that allows to (i) create an almost quantitative conversion of the secondary alcohol into ketone; (ii) reuse said hybrid material in a significant number of consecutive catalytic cycles without activity loss; (iii) eliminate the use of organic solvents; and (iv) reduce significantly the reaction time to 1 h.

Thus, the process for production now developed, due to the use of the above-mentioned hybrid material, looks very promising in the economic point of view and with great potential to be industrially applied, as it allows to overcome the disadvantages of the systems known so far, such as the need for i) high amounts of catalyst [16,17], ii) long reaction times [18-20], iii) presence of additives or co-catalysts [2,16-20], iv) high amounts of toxic oxidants [13-15,21,22] v) solvents [19-24]; or the formation of by-products. Moreover, the known catalysts are frequently difficult to prepare, do not show good activity in the oxidation of aliphatic alcohols and are not possible to reuse [2,4,18-20,25,26].

Additionally, the process for production disclosed in the present invention, due to the use of the above-mentioned hybrid material, is also active in the oxidation of o-, m- or p-cresols, linear alcohols, such as 1-butanol, 2-butanol, 2-hexanol, and diols (e.g., 1,3-butanediol), allowing also the reuse of said hybrid material in a significant number of consecutive catalytic cycles without activity loss.

In a preferred embodiment of the present invention, the hybrid material has an iron content of 2% (w/w).

In another preferred embodiment of the present invention, the temperature used is 80° C.

Solvents and reagents were commercially acquired (Aldrich) and used as received.

The dichlorohydrotris(pyrazol-1-yl)methane iron (II) complex was prepared according to the process described in the literature [27] and the multi-walled carbon nanotubes were functionalized by treatment with 5 M nitric acid for 3 h followed by 20 mM sodium hydroxide for 1 h, according to methods known in the art [29-31]. The hybrid material of the present invention was obtained by heterogenization of the dichlorohydrotris(pyrazol-1-yl)methane iron (II) complex in functionalized multi-walled carbon nanotubes, carried out according to a known protocol [32].

The products of the catalytic assays were analysed by gas chromatography (GC) using a FISONS Instruments GC 8000 series gas chromatograph with a DB-624 capillary column (J&W) (FID detector) and Jasco-Borwin v.1.50 software. The injection temperature was 240° C. The initial temperature was kept at 100° C. for 1 minute, then increased at 10° C./min up to 180° C. and kept at this temperature for 1 minute. Helium was used as carrier gas. The GC-MS analyses were carried out using a Perkin Elmer Clarus 600 C instrument (helium as carrier gas). The ionization voltage was 70 eV. The gas chromatography was carried out in the temperature programming mode, using a SGE BPX5 column (30 m×0.25 mm×0.25 μm). The reaction products were identified by comparison of their retention times with known reference compounds, and by comparison of their mass spectra with the fragment standards obtained from the NIST spectral library stored in the mass spectrometer computer program.

The hybrid material formed by the dichlorohydrotris(pyrazol-1-yl)methane iron (II) complex covalently bound to multi-walled carbon nanotubes functionalized with superficial carboxylate groups, with an iron content of 2% (w/w) is remarkably effective and selective in the microwave-assisted oxidation of secondary alcohols into respective ketones with tert-butyl hydroperoxide, and without solvent addition.

EXAMPLES

The description of the catalytic process of oxidation of the secondary alcohols cyclohexanol, 3-hexanol and 1-phenylethanol is described with more detail by the following examples, for illustrative purposes only, and non-limiting of the scope of the present invention.

Example 1

Process of Microwave-Assisted Peroxidative Oxidation of Cyclohexanol to Cyclohexanone Using as Catalyst the Hybrid Material Formed by the dichlorohydrotris(pyrazol-1-yl)methane Iron (II) Complex Covalently Bound to Multi-Walled Carbon Nanotubes Functionalized with Superficial Carboxylate Groups, with an Iron Content of 2% (w/w)

In a pyrex cylindrical tube of the Monowave 300 Anton Paar microwave reactor the substrate (cyclohexanol, 5 mmol), 70% aqueous solution of tert-butyl hydroperoxide (10 mmol) and 5 μmol of catalyst (based on the iron complex; 0.1% mol vs. substrate) were placed. The system was closed, stirred and microwave irradiated for 60 minutes, up to 80° C., at 25 W of power. After the reaction, the reaction mixture was left to cool down to room temperature.

Extraction and analysis by gas chromatography: The resulting reaction mixture was treated with 5 mL of acetonitrile and 300 μL of internal standard (ex., benzaldehyde). It was stirred for 10 minutes and, after aging, a sample (4 μL) from the organic phase was taken and analysed by GC (or CC-MS) using the internal standard method.

TABLE 1

Microwave-assisted oxidation of cyclohexanol catalysed by hybrid material made of dichlorohydrotris(pyrazol-1-yl)methane iron (II) complex covalently bound to multi-walled carbon nanotubes functionalized with superficial carboxylate groups, with an iron content of 2% (w/w).[a]

| Catalytic cycle | Yield[b]/% | TOF[c]/h$^{-1}$ | Selectivity[d]/% |
|---|---|---|---|
| 1 | 98.3 | 984 | 99 |
| 2 | 97.8 | 978 | 99 |
| 3 | 97.7 | 977 | 99 |
| 4 | 97.7 | 977 | 99 |
| 5 | 97.6 | 976 | 98 |
| 6 | 94.1 | 941 | 96 |
| 7 | 88.4 | 884 | 97 |

[a]Reaction conditions: 5 mmol of substrate, 5 μmol of catalyst (based on the iron complex; 0.1 mol vs. substrate), 10 mmol of tert-butyl hydroperoxide (2 eq., 70% in H$_2$O), 80° C., 60 minutes with microwave irradiation (25 W).
[b]Based on gas chromatography analyses, moles of ketone per 100 moles of alkane, 100% of selectivity in all cases.
[c]Frequency of catalytic cycles = number of moles of ketone per of catalyst per hour.
[d]Moles of ketone per mole of converted alcohol.

Example 2

Process of Microwave-Assisted Peroxidative Oxidation of 1-Phenylethanol to Acetophenone Using as Catalyst the Hybrid Material Formed by the dichlorohydrotris(pyrazol-1-yl)methane Iron (II) Complex Covalently Bound to Multi-Walled Carbon Nanotubes Functionalized with Superficial Carboxylate Groups, with an Iron Content of 2% (w/w)

In a pyrex cylindrical tube of the Monowave 300 Anton Paar microwave reactor the substrate (1-phenylethanol, 5 mmol), 70% aqueous solution of tert-butyl hydroperoxide (10 mmol) and 5 μmol of catalyst (based on the iron complex; 0.1% mol vs. substrate) were placed. The system was closed, stirred and microwave irradiated for 60 minutes, up to 80° C., at 25 W of power. After the reaction, the reaction mixture was left to cool down to room temperature.

Extraction and analysis by gas chromatography: The resulting reaction mixture was treated with 5 mL of acetonitrile and 300 μL of internal standard (ex., benzaldehyde). It was stirred for 10 minutes and, after aging, a sample (4 μL) from the organic phase was taken and analysed by GC (or GC-MS) using the internal standard method.

TABLE 2

Microwave-assisted oxidation of 1-phenylethanol catalysed by hybrid material made of dichlorohydrotris(pyrazol-1-yl)methane iron(II) complex covalently bound to multi-walled carbon nanotubes functionalized with superficial carboxylate groups, with an iron content of 2% (w/w).[a]

| Catalytic cycle | Yield[b]/% | TOF[c]/h$^{-1}$ | Selectivity[d]/% |
|---|---|---|---|
| 1 | 94.2 | 942 | 98 |
| 2 | 93.5 | 935 | 98 |
| 3 | 93.3 | 933 | 98 |
| 4 | 93.3 | 933 | 98 |
| 5 | 92.8 | 928 | 97 |
| 6 | 92.1 | 921 | 97 |

[a]Reaction conditions: 5 mmol of substrate, 5 μmol of catalyst: (based on the iron complex; 0.1% mol vs. substrate), 10 mmol of tert-butyl hydroperoxide (2 eq., 70% in H$_2$O), 80° C., 60 minutes with microwave irradiation (25 W).
[b]Based on gas chromatography analyses, moles of ketone per 100 moles of alkane, 100% of selectivity in all cases.
[c]Frequency of catalytic cycles = number of moles of ketone, per moles of catalyst per hour.
[d]Moles of ketone per mole of converted alcohol.

Example 3

Process of Microwave-Assisted Peroxidative Oxidation of 3-Hexanol to 3-Hexanone Using as Catalyst the Hybrid Material Formed by the dichlorohydrotris(pyrazol-1-yl)methane Iron (II) Complex Covalently Bound to Multi-Walled Carbon Nanotubes Functionalized with Superficial Carboxylate Groups, with an Iron Content of 2% (w/w)

In a pyrex cylindrical tube of the Monowave 300 Anton Paar microwave reactor the substrate (3-hexanol, 5 mmol), 70% aqueous solution of tert-butyl hydroperoxide (10 mmol) and 5 μmol of catalyst (based on the iron complex; 0.1% mol vs. substrate) were placed. The system was closed, stirred and microwave irradiated for 60 minutes, up to 80° C., at 25 W of power. After the reaction, the reaction mixture was left to cool down to room temperature.

Extraction and analysis by gas chromatography: The resulting reaction mixture was treated with 5 mL of acetonitrile and 300 μL of internal standard (ex., benzaldehyde). It was stirred for 10 minutes and, after aging, a sample (4 μL) from the organic phase was taken and analysed by GC (or GC-MS) using the internal standard method.

3-Hexanone was obtained as the sole product (100% of selectivity) with a 9.8% yield and TOF of 98 h$^{-1}$. The excellent selectivity obtained with the present process for partial oxidation of the substrate 3-hexanol is worthy of note.

REFERENCES

[1] A. Pombeiro (Ed.), *Advances in Organometallic Chemistry and Catalysis, The Silver/Gold Jubilee ICOMC Celebratory Book*, J. Wiley & Sons, 2014.
[2] M. N. Kopylovich, A. P. C. Ribeiro, E. C. B. A. Alegria, N. M. R. Martins, L. M. D. R. S. Martins, A. J. L. Pombeiro, *Adv. Organomet. Chem.*, 2015, 63, Ch. 3, 91-174.
[3] L. Martins, A. Pombeiro, *Coord. Chem. Rev.*, 2014, 265, 74.
[4] M. Sutradhar, L. M. D. R. S. Martins, M. F. C. Guedes da Silva, A. J. L. Pombeiro, *Coord. Chem. Rev.*, 2015, 301-302, 200-239.
[5] K. Weissermel, H.-J. Arpe, *Industrial Organic Chemistry*, 2$^{nd}$ ed., VCH Press, Weinheim, 1993.
[6] R. Whyman, *Applied Organometallic Chemistry and Catalysis*, Oxford University Press, Oxford, 2001.

[7] J.-E. Bäckvall, *Modern Oxidation Methods*, Wiley-VCH, Weinheim, 2004.
[8] R. A. Sheldon, I. Arends, U. Hanefeld, *Green Chemistry and Catalysis*, Wiley-VCH, Weinheim, 2007.
[9] G. P. Chiusoli, P. M. Maitlis (Eds.), *Metal-catalysis in Industrial Organic Processes*, Royal Society of Chemistry, Cambridge, 2006.
[10] P. T. Anastas, J. C. Warner, *Green Chemistry: Theory and Practice*, Oxford University Press, Oxford, U.K., 1998.
[11] P. T. Anastas, M. Kirchhoff, *Acc. Chem. Res.*, 2002, 35, 686.
[12] R. A. Smiley, H. L. Jackson, *Chemistry and the Chemical Industry*, CRC Press, 2002.
[13] *Ullmann's Encyclopedia of Industrial Chemistry*, Wiley-VCH, Weinheim, 6$^{th}$ edn., 2002.
[14] R. A. Smiley, H. L. Jackson, *Chemistry and the Chemical Industry*, CRC Press, 2002.
[15] *Process Chemistry in the Pharmaceutical Industry*. Vol. 2, ed. K. Gadamasetti, T. Braish, CRC Press, 2008.
[16] I. E. Markó, P. R. Giles, M. Tsukazaki, S. M. Brown, C. J. Urch, *Science* 1996, 274, 2044.
[17] D. Bogda, M. Lukasiewicz, *Synlett*, 2000, 143.
[18] G. Ferguson, A. N. Ajjou, *Tetrahedron Lett.*, 2003, 44, 9139.
[19] G. Rothenberg, L. Feldberg, H. Wiener, Y. Sasson, *J. Chem. Soc., Perkin Trans.*, 1998, 2, 2429.
[20] R. Chakrabarty, P. Sarmah, B. Saha, S. Chakravorty, B. K. Das, *Inorg. Chem.* 2009, 48, 6371.
[21] J. Singh, M. Shana, M. Chibber, J. Kaur, G. L. Kad, *Synth. Commun.*, 2000, 30, 3941.
[22] D. Pandey, D. S. Kotari, *Oxyd. Commun.*, 2009, 32, 371.
[23] L. Palombi, F. Bonadies, A. Scetti, *Tetrahedron*, 1997, 53, 15867.
[24] C. González-Arellano, J. M. Campelo, D. J. Macquarrie, J. M. Marinas, *ChemSusChem.*, 2008, 1, 746.
[25] A. Corma, H. Garcia, *Chem. Soc. Rev.*, 2008, 37, 2096.
[26] L. Tonucci, M. Nicastro, N. d'Alessandro, M. Bressan, P. D'Ambrosio, A. Morvillo, *Green Chem.*, 2009, 11, 816.
[27] T. F. S. Silva, E. C. B. A. Alegria, L. M. D. R. S. Martins, A. J. L. Pombeiro, *Adv. Synth. Cat.* 2008, 350, 706.
[28] J. L. Figueiredo, M. F. R. Pereira, M. M. A. Freitas, J. J. M. Órfão, *Carbon*, 1999, 37, 1379.
[29] N. Mahata, M. F. R. Pereira, F. Suárez-García, A. Martínez-Alonso, J. M. D. Tascón, J. L. Figueiredo, *J. Colloid Interface Sci.* 2008, 324, 150.
[30] I. Gerber, M. Oubenali, R. Bacsa, J. Durand, A. Gonçalves, M. F. R. Pereira, F. Jolibois, L. Perrin, R. Poteau, P. Serp, *Chem. Eur. J.*, 2011, 17, 11467.
[31] F. Maia, N. Mahata, B. Jarrais, A. R. Silva, M. F. R. Pereira, C. Freire, J. L. Figueiredo, *J. Mol. Catal. A*, 2009, 305, 135.
[32] L. M. D. R. S. Martins, M. P. Almeida, S. A. C. Carabineiro, J. L. Figueiredo, A. J. L. Pombeiro, *ChemCatChem*, 2013, 5, 3847.

The invention claimed is:

1. A process for production of ketones from secondary alcohols, assisted by microwave radiation comprising the mixture of an oxidising agent with a hybrid, material dichlorohydrotris (pyrazol-1-yl) methane iron (II) covalently bound to multi-walled carbon nanotubes functionalized with superficial carboxylate groups as catalyst, at a temperature of 80° C.

2. The process according to claim 1, wherein the oxidising agent is a 70% aqueous solution of tert-butyl hydroperoxide.

3. The process according to claim 1, wherein the dichlorohydrotris (pyrazol-1-yl) methane iron (II) complex contains an iron content of 2% (w/w).

4. The process according to claim 1, wherein the secondary alcohols are selected from: cyclohexanol, 1-phenylethanol, o-, m- or p-cresols, linear alcohols 2-hexanol, 3-hexanol, 1-butanol or 2-butanol, and diols.

5. The process according to claim 1, wherein the reaction time is one hour.

6. The process according to claim 1, which is free from solvent addition.

7. The process according to claim 1, wherein the catalyst dichlorohydrotris (pyrazol-1-yl) methane iron (II) covalently bound to multiple wall carbon nanotubes functionalized with superficial carboxylate groups is reusable in at least six subsequent catalytic cycles.

* * * * *